(12) United States Patent
Kenmochi et al.

(10) Patent No.: US 7,588,561 B2
(45) Date of Patent: Sep. 15, 2009

(54) PULL-ON DISPOSABLE WEARING ARTICLE WITH TAPERED FOLDING GUIDE LINES AND TUCKING ZONES

(75) Inventors: Yasuhiko Kenmochi, Kagawa-ken (JP); Takaaki Shimada, Kagawa-ken (JP); Takako Uosawa, Kagawa-ken (JP); Toshifumi Otsubo, Kagawa-ken (JP)

(73) Assignee: Uni-Charm Corporation, Ehime-Ken (JP)

( * ) Notice: Subject to any disclaimer, the term of this patent is extended or adjusted under 35 U.S.C. 154(b) by 0 days.

(21) Appl. No.: 10/753,531

(22) Filed: Jan. 9, 2004

(65) Prior Publication Data

US 2005/0075618 A1   Apr. 7, 2005

(30) Foreign Application Priority Data

Jan. 10, 2003   (JP) ............................. 2003-038977

(51) Int. Cl.
*A61F 13/15* (2006.01)
*A61F 13/20* (2006.01)

(52) U.S. Cl. ........................... 604/385.27; 604/385.01; 604/385.28

(58) Field of Classification Search .......... 604/385.101, 604/385.2–385.28, 201, 385.01, 358, 385.201; D24/124, 126

See application file for complete search history.

(56) References Cited

U.S. PATENT DOCUMENTS

| | | | |
|---|---|---|---|
| 3,196,874 A | | 7/1965 | Hrubecky |
| 3,211,147 A | | 10/1965 | Pherson et al. |
| 3,744,494 A | | 7/1973 | Marsan |
| 3,774,610 A | * | 11/1973 | Eckert et al. ................. 604/365 |
| 4,661,102 A | * | 4/1987 | Shikata et al. .......... 604/385.25 |
| 4,695,278 A | * | 9/1987 | Lawson .................. 604/385.27 |
| 4,966,286 A | | 10/1990 | Muckenfuhs |
| 5,036,978 A | | 8/1991 | Frank et al. |
| 5,054,619 A | | 10/1991 | Muckenfuhs |
| 5,282,687 A | | 2/1994 | Yee |
| 5,361,905 A | | 11/1994 | McQueeny et al. |
| 5,746,730 A | * | 5/1998 | Suzuki et al. ........... 604/385.26 |
| 5,814,036 A | * | 9/1998 | Ronnberg et al. ..... 604/385.201 |
| 5,934,470 A | | 8/1999 | Bauer et al. |

(Continued)

FOREIGN PATENT DOCUMENTS

EP   0951886   10/1999

(Continued)

*Primary Examiner*—Michele Kidwell
(74) *Attorney, Agent, or Firm*—Lowe Hauptman Ham & Berner

(57) ABSTRACT

A pull-on disposable wearing article is formed in a crotch region with first and second pairs of folding guide lines extending from first and second waist lateral margins toward a transverse middle of the crotch region, respectively. The crotch region is divided into a first zone enclosed by the first waist lateral margin and the first folding guide lines, a second zone enclosed by the second waist lateral margin and the second folding guide lines and a third zone outside the first and second zones. Inside the side edges of the core, first and second elastic members are contractible attached to the article. The first and second elastic members extend across the first and second zones to the third zone. The first and second zones are pulled inward under contractile forces of the elastic members to form tucks which are convex inwardly of the leg-holes.

20 Claims, 8 Drawing Sheets

U.S. PATENT DOCUMENTS

| | | |
|---|---|---|
| 5,967,665 A | 10/1999 | MacDonald et al. |
| 6,079,562 A | 6/2000 | Bauer et al. |
| 6,165,160 A * | 12/2000 | Suzuki et al. ......... 604/385.201 |
| 6,666,851 B2 * | 12/2003 | Otsubo et al. ......... 604/385.201 |
| 2004/0133178 A1 * | 7/2004 | Otsubo et al. .......... 604/385.01 |

FOREIGN PATENT DOCUMENTS

| | | | |
|---|---|---|---|
| EP | 951890 A2 | * | 10/1999 |
| EP | 988846 A2 | * | 3/2000 |
| EP | 1346713 A2 | * | 9/2003 |
| GB | 2253131 | | 9/1992 |
| JP | 47-36734 | | 12/1972 |
| JP | 48-20638 | | 3/1973 |
| JP | 50-21845 | | 3/1975 |
| JP | 5-76565 | | 3/1993 |
| JP | 11-104177 | | 4/1999 |
| JP | 11-155904 | | 6/1999 |
| JP | 2000-51273 | | 2/2000 |
| JP | 2002-35033 | | 2/2002 |

* cited by examiner

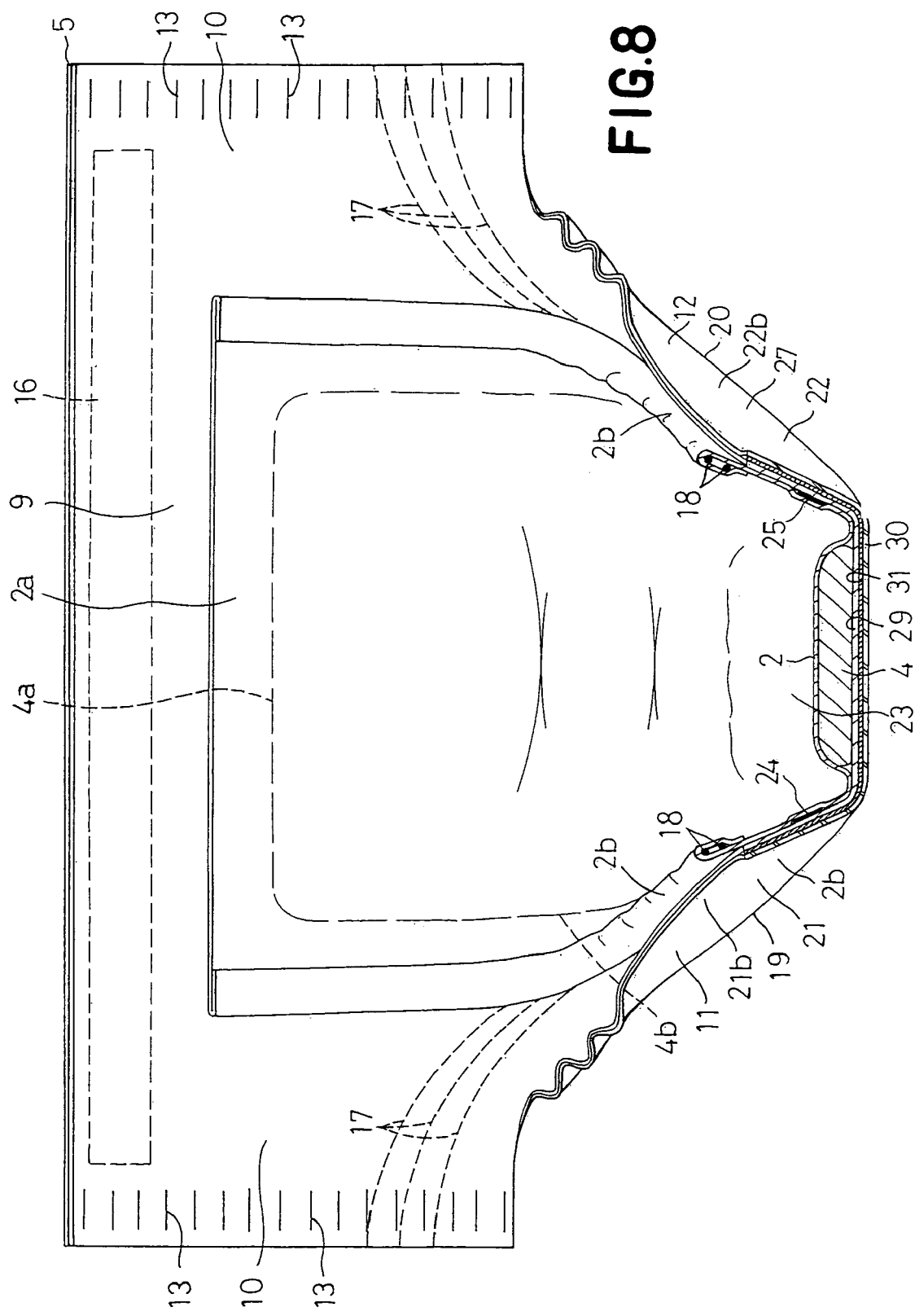

PULL-ON DISPOSABLE WEARING ARTICLE WITH TAPERED FOLDING GUIDE LINES AND TUCKING ZONES

BACKGROUND OF THE INVENTION

The present invention relates to pull-on disposable wearing articles for absorption and containment of bodily discharges. The present application is based on, and claims priority from, Japanese Application Serial Number 2003-38977, filed Jan. 10, 2003, the disclosure of which is hereby incorporated by reference herein in its entirety.

Pull-on disposable wearing articles having front and rear waist regions opposed to each other, a crotch region extending between these waist regions, a waist-hole and a pair of leg-holes are well known, one of which is disclosed in Japanese Patent Application Publication No. 2002-35033A. This article comprises a liquid-pervious sheet, a liquid-impervious sheet and a liquid-absorbent core interposed between these sheets and extending over the crotch region and further into the front and rear waist regions. The crotch region is formed with tucks which are convex inwardly of the respective leg-holes.

The above-cited article has a waist-surrounding upper end margin defined by the front and rear waist regions and extending in a transverse direction, waists' lateral margins defined also by the front and rear waist regions and extending in a longitudinal direction and a pair of leg-surrounding lateral margins defined by the crotch region and extending in a leg-surrounding direction. The waists' lateral margins put flat together are joined one to another by means of plural welding lines arranged intermittently in the longitudinal direction. This article is formed with a pair of folding guide lines extending between the transversely opposite leg-surrounding lateral margins and intersecting at a transversely middle point in the crotch region. Thus the crotch region is divided into first and second zones enclosed by the leg-surrounding lateral margins and these folding guide lines, respectively, and a third zone except the first and second zones. The first and second zones are folded along the respective folding guide lines between front and rear halves of the third zone so as to form a pair of tucks which are convex inwardly of the respective leg-holes. Compared to the state before the first and second zones are folded inward, the transverse dimension of the crotch region can be effectively reduced by folding these zones between the front and rear halves of the third zone.

However, the above-cited article has been accompanied with the problem such that the tucks are unfolded along the folding guide lines as the article wearer's legs are guided through the leg-holes of the article and the transverse dimension of the crotch region returns to the dimension before these tucks have been formed. In a consequence, the transverse dimension sometimes becomes larger than the wearer's crotch region and can not be appropriately received in the wearer crotch region. The core becomes more bulky than supposed from its predetermined thickness and stiffness and create a feeling of discomfort against the wearer. In addition, the core laid in the crotch region is irregularly folded or the core is formed with a plurality of irregular wrinkles and deteriorates bodily discharge absorbing function excepted for the crotch region, causing any quantity of bodily discharges to leak sideways from the crotch region.

SUMMARY OF THE INVENTION

It is an object of the present invention to provide a pull-on disposable wearing article allowing a crotch region to be formed with tucks stabilized against being unintentionally unfolded, which serve, in turn, to reduce a transverse dimension of the crotch region so that the crotch region may be compactly received in a crotch region of the article wearer.

According to the present invention, there is provided a pull-on disposable wearing article having front and rear waist regions opposed to each other and a crotch region extending between these waist regions and a waist-surrounding upper end margin defined by the front and rear waist regions and extending in a transverse direction, transversely opposite waist lateral margins defined by the front and rear waist regions and extending in a longitudinal direction so that the waist lateral margins of the front and rear waist regions are connected to for a waist-hole and a pair of leg-holes, first and second leg-surrounding lateral margins defined by the crotch region and extending in a leg-surrounding direction, and a liquid-absorbent core laid in the front waist region, the rear waist region and the crotch region, or at least in the crotch region.

The article further comprises the following features:

The crotch region is formed with a pair of first folding-guide lines extending from two points on the first leg-surrounding lateral margin placed aside toward the front and rear waist regions, respectively, toward a transverse middle of the crotch region and a pair of second folding guide lines extending from two points on the second leg-surrounding lateral margin placed aside toward the front and rear waist regions, respectively, toward the transverse middle of the crotch region so that the crotch region are divided into a first zone enclosed by the first leg-surrounding lateral margin and the first folding guide lines so as to taper toward the transverse middle of the crotch region, a second zone enclosed by the second leg-surrounding lateral margin and the second folding guide lines so as to taper toward the transverse middle of the crotch region and a third zone except the first and second zones.

A first elastic member extending in the leg-surrounding direction across the first zone to the third zone is contractibly attached to the article immediately inside the side edge of the core on the side of the first leg-surrounding lateral margin and a second elastic member extending in the leg-surrounding direction across the second zone to the third zone is contractibly attached to the article immediately inside the side edge of the core on the side of the second leg-surrounding lateral margin.

The first zone is pulled inward as viewed in the leg-surrounding direction under a contractile force of the first elastic member to form a tuck which is convex inwardly of the leg-hole and the second zone is pulled inward as viewed in the leg-surrounding direction under a contractile force of the second elastic member to form a tuck which is convex inwardly of the leg-hole.

The invention includes the following embodiments.

The first and second elastic members exhibit a contraction percentage in a range of 25 to 70% on the basis of 100 representing a length of the first and second elastic members having been stretched at a predetermined ratio.

The first and second elastic members exhibit a stretch stress in a range of 0.1 to 3.0 N.

The core has stiffness lower in the first and second zones than in the third zone.

The core is absent in the first and second zones.

The article comprises a liquid-pervious sheet facing a wearer's body, a liquid-impervious sheet facing away from the wearer's body and the core interposed between these sheets.

BRIEF DESCRIPTION OF THE DRAWINGS

FIG. 8 is a sectional view taken along the line VIII-VIII in FIG. 5.

DETAILED DESCRIPTION OF THE PREFERRED EMBODIMENTS

Details of a pull-on disposable wearing article according to the present invention will be more fully understood from the description given hereunder with reference to the accompanying drawings.

Figure 1:
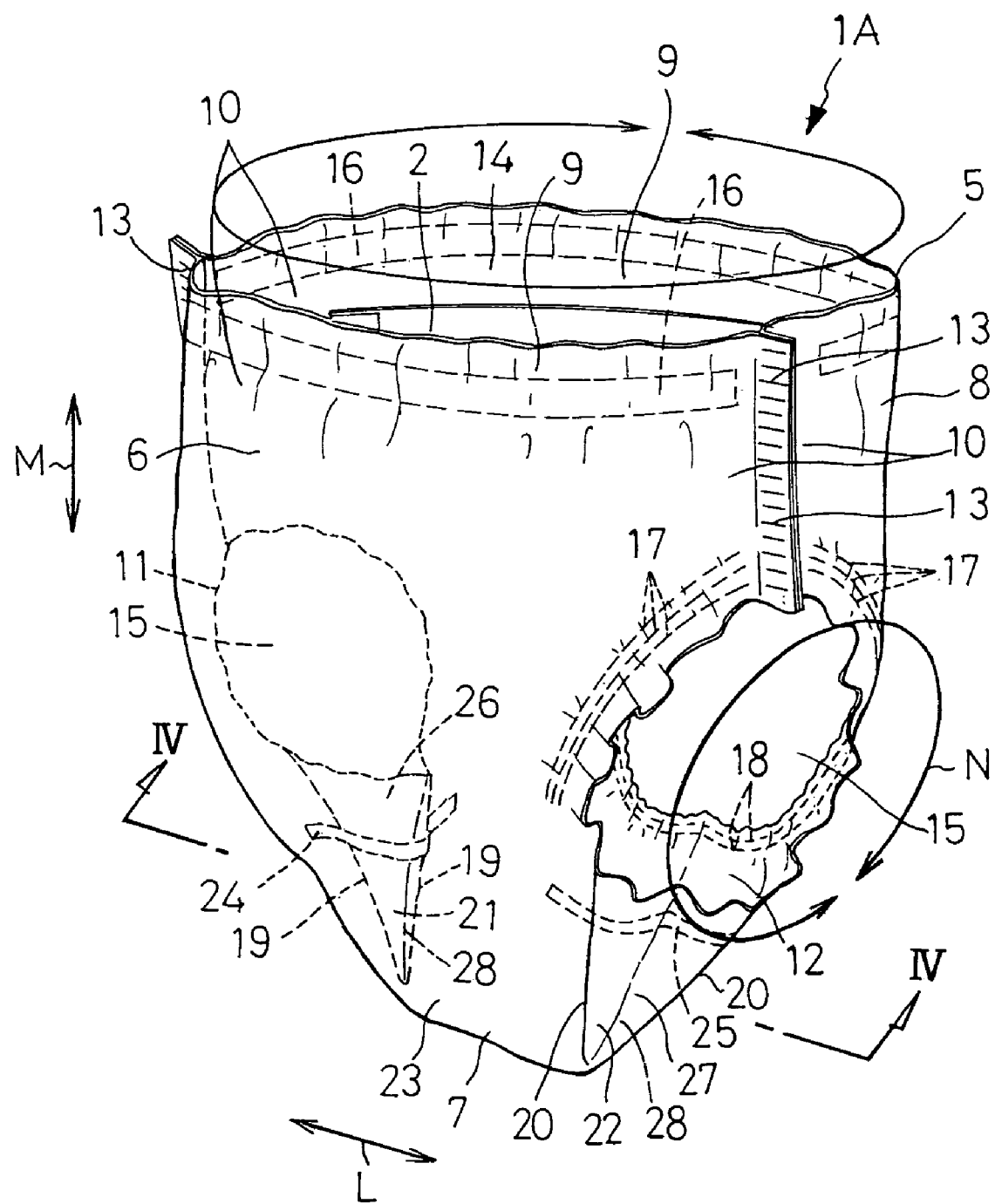
FIG. 1 is a perspective view showing a first embodiment of a pull-on disposable wearing article according to the invention.
Figure 2:
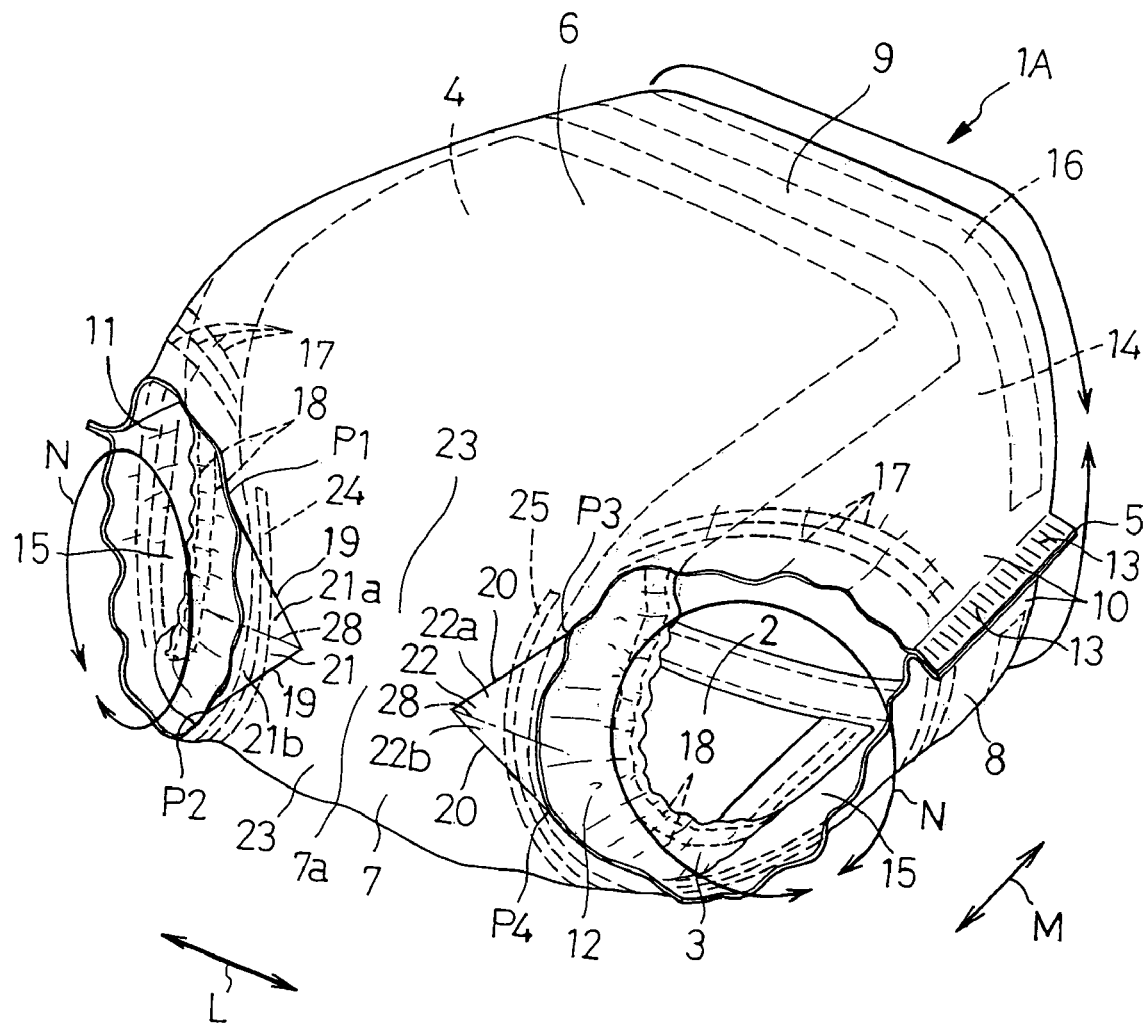
FIG. 2 is a perspective view showing the article of FIG. 1 as tucked regions unfolded outward against contractile force of elastic members.
Figure 3:
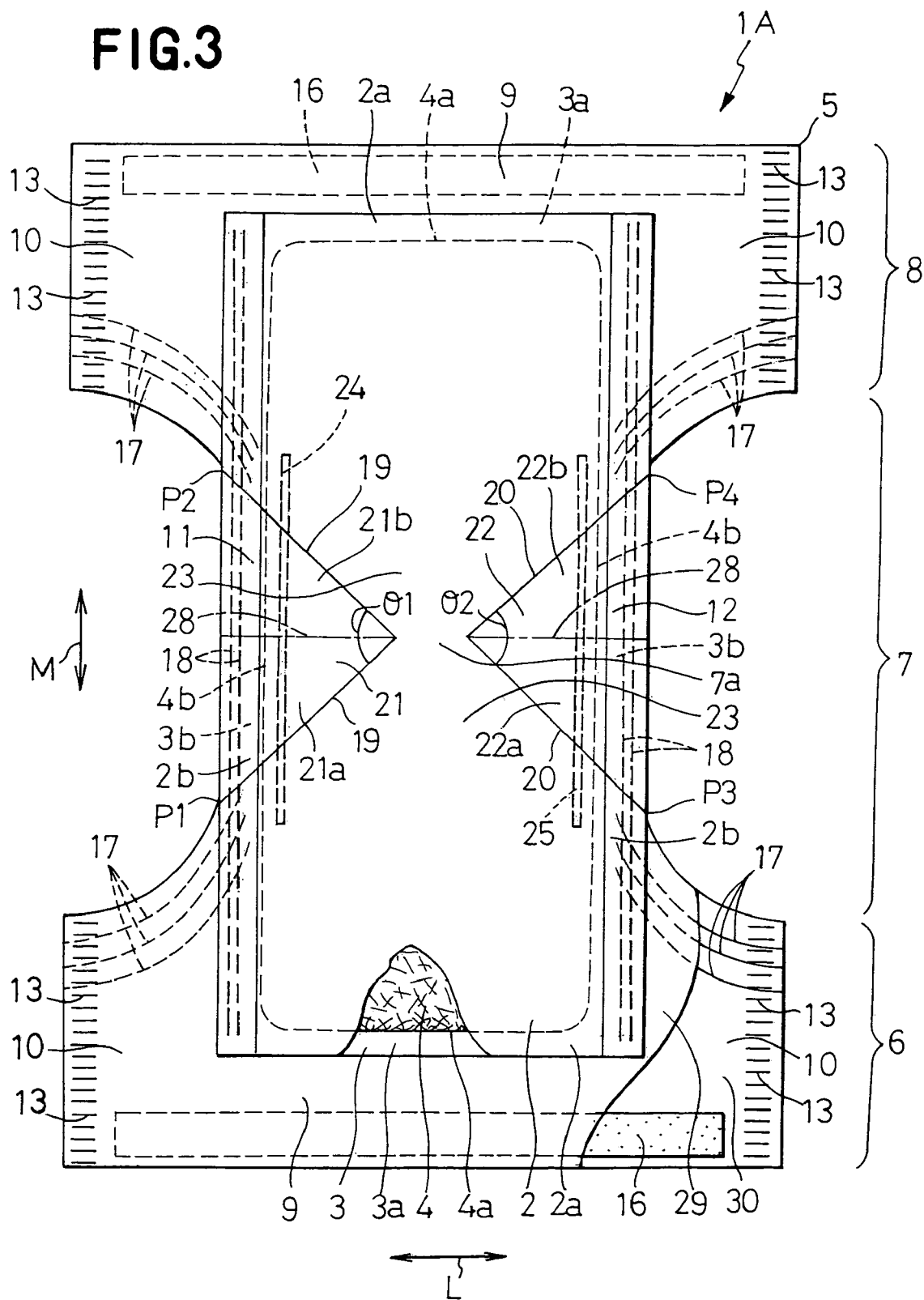
FIG. 3 is a partially cutaway developed plan view showing the article of FIG. 1 with front and rear waist regions disconnected from each other.
Figure 4:
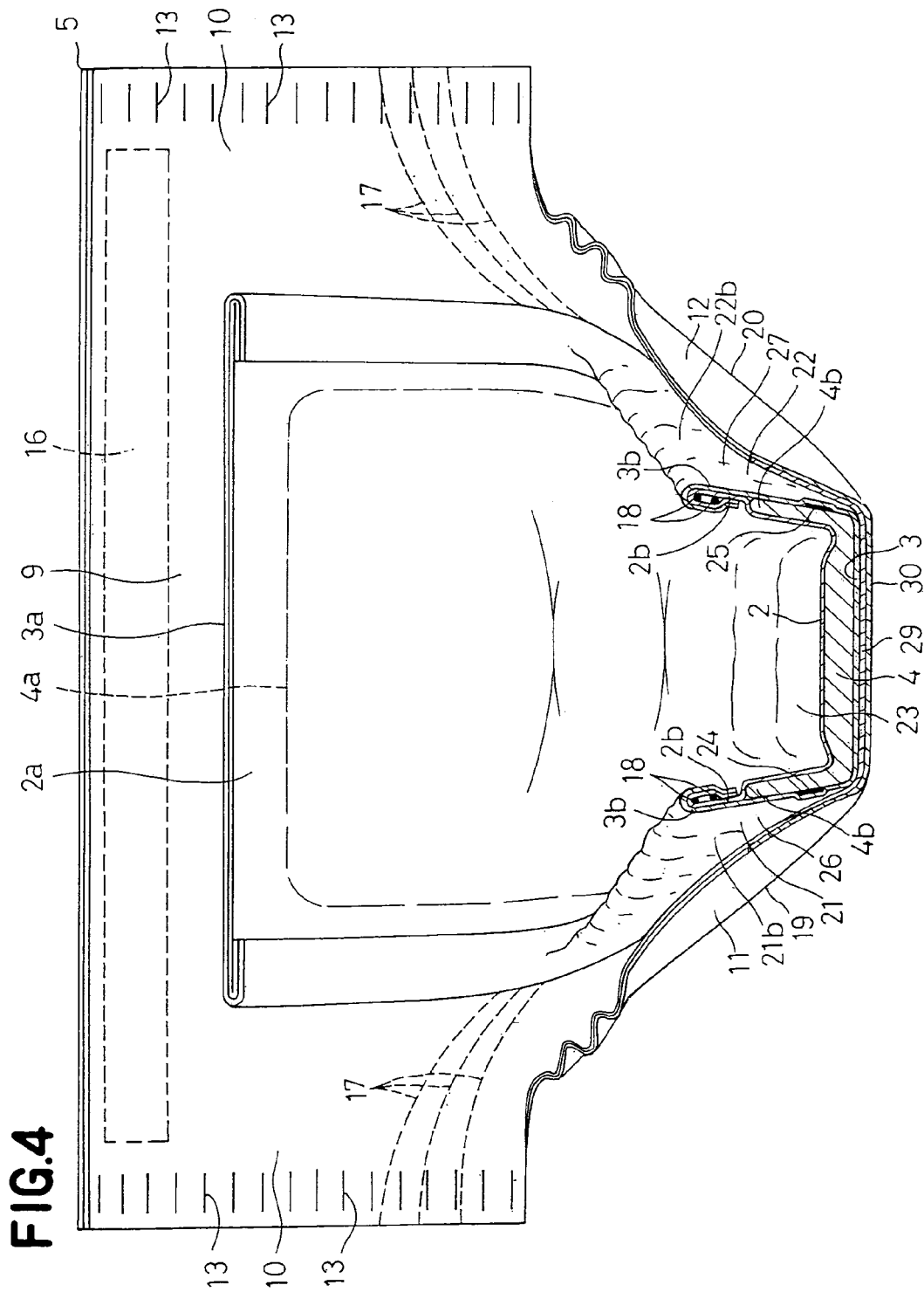
FIG. 4 is a sectional view taken along the line IV-IV in FIG. 1.

FIG. 1 is a perspective view showing a wearing article 1A according to an embodiment of the invention, FIG. 2 is a perspective view showing the article 1A of FIG. 1 as tucks 26, 27 unfolded outward against contractile force of elastic members 24, 25, FIG. 3 is a developed plan view showing the article 1A of FIG. 1 with waist lateral margins 10 disconnected from each other as partially broken away, and FIG. 4 is a sectional view taken along the line IV-IV in FIG. 1. In FIGS. 1 through 3, a transverse direction is indicated by an arrow L, a longitudinal direction is indicated by an arrow M and a leg-surrounding direction is indicated by an arrow N (only in FIGS. 1 and 2). FIG. 3 shows the article 1A as stretched in the transverse direction as well as in the longitudinal direction. Expression used herein "inner surfaces" of a topsheet 2, an intermediate sheet 3 and an outer sheet 5 refers to the surfaces of these sheets facing a core 4 and expression used herein "outer surfaces" of these sheets 2, 3, 5 refers to the surfaces thereof facing away from the core 4.

The article 1A comprises the liquid-pervious topsheet 2 (liquid-pervious sheet), the intermediate sheet 3, the liquid-absorbent core 4 interposed between these sheets 2, 3, the liquid-impervious outer sheet 5 (liquid-impervious sheet) laid outside the intermediate sheet 3, and respective elastic members 16, 17, 18, 24, 25. The topsheet 2 faces a wearer's body with interposition of the core 4 and the intermediate sheet 3 as well as the outer sheet 5 face away from a wearer's body. The article 1A has a front waist region 6 and a rear waist region 8 opposed to each other and a crotch region 7 extending between these waist regions 6, 8. The core 4 extends over the crotch region 7 and further into the front and rear waist regions 6, 8 so as to occupy transverse middle areas in these front and rear waist regions 6, 8.

The article 1A has a waist-surrounding upper margin 9 defined by respective portions of the front and rear waist regions 6, 8 extending outside longitudinally opposite ends 4a of the core 4 in the transverse direction, transversely opposite waist lateral margins 10 defined by respective portions of the front and rear waist regions 6, 8 extending outside transversely opposite side edges 4b of the core in the longitudinal direction, and first and second leg-surrounding lateral margins 11, 12 defined by respective portions of the crotch region 7 extending outside the transversely opposite side edges 4b of the core 4 in the leg-surrounding direction. The first and second leg-surrounding lateral margins 11, 12 describe circular arcs which are convex inward as viewed in the transverse direction of the article 1A. Thus the article 1A presents a generally hourglass-like planar shape.

The waist lateral margins 10 are overlapped and joined together by means of plural welding lines 13 arranged intermittently in the longitudinal direction. The article 1A is formed with a waist-hole 14 surrounded by the waist-surrounding upper margin 9 and a pair of leg-holes 15 surrounded by the first and second leg-surrounding lateral margins 11, 12, respectively.

A belt-like waist elastic member 16 extending in the transverse direction is contractibly attached to the waist-surrounding upper margin 9. Plural leg elastic members 17, 18 are contractibly attached to the first and second leg-surrounding lateral margins 11, 12, respectively, so as to extend in the leg-surrounding direction.

As shown by FIGS. 2 and 3, the crotch region 7 is formed with a pair of first folding guide lines 19 extending in the transverse direction from two points P1, P2 on the first leg-surrounding lateral margin 11 placed aside toward the front and rear waist regions 6, 8, respectively, toward a transverse middle 7a of the crotch region 7 and a pair of second folding guide lines 20 extending in the transverse direction from two points P3, P4 on the second leg-surrounding lateral margin 12 placed aside toward the front and rear waist regions 6, 8, respectively, toward the transverse middle 7a of the crotch region 7. The first folding guide lines 19 describe a generally V-shape broadening from the middle 7a of the crotch region 7 toward the first leg-surrounding lateral margin 11 and the second folding guide lines 20 describe a generally V-shape broadening from the middle 7a of the crotch region 7 toward the second leg-surrounding lateral margin 12.

The crotch region 7 is divided into a first zone 21 enclosed by the first leg-surrounding lateral margin 11 and the first folding guide lines 19, a second zone 22 enclosed by the second leg-surrounding lateral margin 12 and the second folding guide lines 20 and a third zone 23 except the first and second zones 21, 22. The first zone 21 has a generally triangular shape tapering from the first leg-surrounding lateral margin 11 toward the middle 7a of the crotch region 7. Similarly, the second zone 22 presents a generally triangular shape tapering from the second leg-surrounding lateral margin 12 toward the middle 7a of the crotch region 7. Stiffness of the core 4 is lower in the first and second zones 21, 22 than in the third zone 23.

Immediately inside the side edge 4b of the core 4 on the side of the first leg-surrounding lateral margin 11, a first elastic member 24 stretched at a predetermined ratio is contractibly attached to the article. The first elastic member 24 is laid inside the leg elastic members 17, 18 as viewed in the transverse direction and extends in the leg-surrounding direction across the first zone 21 to the third zone 23. In the similar manner, immediately inside the side edge 4b of the core 4 on the side of the second leg-surrounding lateral margin 12, a second elastic member 25 stretched at a predetermined ratio is contractibly attached to the article. The second elastic member 25 is laid inside the leg elastic members 17, 18 as viewed in the transverse direction and extends in the leg-surrounding direction across the second zone 22 to the third zone 23. The first and second elastic members 24, 25 are interposed between the topsheet 2 and the core 4 and joined thereto.

In the crotch region 7, the first zone 21 is pulled inward as viewed in the leg-surrounding direction under the contractile force of the first elastic member 24 and the second zone 22 is pulled inward as viewed in the leg-surrounding direction under the contractile force of the second elastic member 25 so that the crotch region 7 is folded along the first and second folding guide lines 19, 20. In the crotch region 7, consequently, the first zone 21 forms a tuck 26 which is convex inwardly of the leg-hole 15 and the second zone 22 forms a tuck 27 which is convex inwardly of the leg-hole 15. The first zone 21 and the second zone 22 are tucked between front and rear halves of the third zone 23. In the first zone 21, a front half 21a and a rear half 21b thereof contact each other while portions of the outer sheet 5 extending in these front and rear halves 21a, 21b of the first zone 21 have respective outer surfaces contacting each other. In the second zone 22 a front half 22a and a rear half 22b thereof contact each other while portions of the outer sheet 5 extending in these front and rear halves 22a, 22b of the second zone 22 have respective outer surfaces contacting each other. In the first and second zones 21, 22, imaginary third folding guide lines 28 extending in the transverse direction are defined between the front and rear halves 21a, 21b and between the front and rear halves 22a, 22b, respectively. An alternative case may be also assumed in which the zones 21, 22 are pulled inward as viewed in the leg-surrounding direction under the contractile force of the first and second elastic members 24, 25 and thereby these zones 21, 22 are tucked inwardly of the respective leg-holes 15 without forming the third folding guide lines 28 in these first and second zones 21, 22.

The first and second elastic members 24, 25 exhibit a contraction percentage in a range of 25 to 70% on the basis of 100 representing the length of these elastic members 24, 25 having been stretched at a predetermined ratio, and exhibit a stretch stress in a range of 0.1 to 3.0 N. The contraction percentage is calculated from formula:

$$\{(A-B)/A\} \times 100$$

where A represents length of the elastic members 24, 25 stretched at a predetermined ratio and B represents length of these elastic members 24, 25 after contracted.

If the contraction percentage of the elastic members 24, 25 is less than 25%, the elastic members 24, 25 after contracted from stretched state sometimes can not sufficiently pull the first and second zones 21, 22 inward as viewed in the leg-surrounding direction to form the tucks 26, 27 in the crotch region 7. If the stretch stress of the elastic members 24, 25 is less than 0.1 N, the contractile force of the elastic members 24, 25 will sometimes be insufficient to maintain the tucks 26, 27, so the tucks 26, 27 may be easily unfolded along the first and second folding guide lines 19, 20 as the article 1A is put on the wearer's body. In consequence, the crotch region 7 may return to it initial state prior to the formation of the tucks 26, 27.

Both the topsheet 2 and the intermediate sheet 3 has generally rectangular planar shapes extend over the front waist region 6, the crotch region 7 and the rear waist region 8. These sheets 2, 3 respectively have longitudinally opposite end margins 2a, 3a extending outward beyond the longitudinally opposite ends 4a of the core 4 and transversely opposite lateral margins 2b, 3b extending outward beyond the transversely opposite side edges 4b of the core 4. Inner surfaces of these sheets 2, 3 are overlapped and joined together along these end margins 2a, 3a and these lateral margins 2b, 3b. In the front and rear waist regions 6, 8, the lateral margins 2b, 3b of these sheets 2, 3 are folded inward as viewed in the transverse direction onto the upper surface of the core 4 and the lateral margins 2b of the sheet 2 are joined to the end margins 2a thereof. The intermediate sheet 3 has its outer surface joined to the inner surface of the outer sheet 5. The core 4 is joined to the respective inner surfaces of the topsheet 2 and the intermediate sheet 3.

The outer sheet 5 comprises two hydrophobic fibrous nonwoven fabric layers 29, 30 laminated one upon another. The outer sheet 5 has a surface area larger than those of the topsheet 2 and the intermediate sheet 3 and has a generally hourglass-like planar shape. The waist-surrounding upper end margin 9 and the waist lateral margins 10 are formed from the outer sheet 5 and the leg-surrounding lateral margins 11, 12 are formed by the lateral margins 2b, 3b of the sheets 2, 3 and the outer sheet 5.

The waist elastic member 16 is interposed between the nonwoven fabric layers 29, 30 constituting the outer sheet 5 and bonded to these nonwoven fabric layers 29, 30. The leg elastic members 17, 18 comprise the elastic member 17 attached to the outer sheet 5 and the elastic member 18 attached to the topsheet 2 and the intermediate sheet 3. The elastic member 17 is interposed between the nonwoven fabric layers 29, 30 and bonded to these nonwoven fabric layers 23, 30. The elastic member 18 is interposed between the topsheet 2 and the intermediate sheet 3 and joined to respective inner surfaces of the lateral margins 2b, 3b thereof. These elastic members 17, 18 extend along the leg-surrounding lateral margins 11, 12 so as to form generally annular shapes.

The core 4 comprises a mixture of fluff pulp and super-absorbent polymer particles or a mixture of fluff pulp, super-absorbent polymer particles and thermoplastic synthetic resin fibers, in any case, compressed to a desired thickness. Therefore, stiffness of the core 4 is higher than those of the topsheet, the intermediate sheet 3 and the outer sheet 5. Preferably, the core 4 is entirely wrapped with a liquid-pervious sheet such as a tissue paper or a hydrophilic fibrous nonwoven fabric in order to prevent the core 4 from getting out of its initial shape and/or in order to prevent polymer particles from falling off.

To adjust stiffness of the core 4 to be lower in the first and second zones 21, 22 than in the third zone 23, a basis weight or a density of the core 4 may be adjusted to be lower in the first and second zones 21, 22 than in the third zone 23.

The article 1A is constructed so that, in the crotch region 7, the first and second zones 21, 22 form the tucks 26, 27 which are convex inwardly of the leg-holes 15 and therefore a transverse dimension of the crotch region 7 can be more easily reduced than in the case of the crotch region 7 not formed with such tucks 26, 27 (See FIG. 2). The contractile force of the first and second elastic members 24, 25 reliably stabilizes the tucks 26, 27 and it is unlikely that these tucks 26, 27 might be unintentionally unfolded even when a wearer's legs are guided through the leg-holes 15.

The crotch region 7 is appropriately received in a wearer's crotch region as the article 1A is put on a wearer's body, so there is no possibility that the crotch region 7 might become excessively bulky and the wearer might experience a feeling of discomfort. In addition, there is no anxiety that the core 4 in the crotch region 7 might be irregularly folded and/or formed with a plurality of irregular wrinkles even if the crotch region 7 is squeezed in a wearer's crotch region. Thus, bodily discharges absorbing function in the crotch region 7 is reliably maintained without any possibility that the bodily discharges might leak sideways from the crotch region 7.

In the article 1A, an angle θ1 defined between the first folding guide lines 19 as well as an angle θ2 defined between the second folding guide lines 20 is preferably in a range of 30 to 120° as shown by FIG. 3. If these angles θ1, θ2 are less than 30°, the first and second zones 21, 22 will become unacceptably narrow and make it impossible to form the tucks sufficiently large to reduce the transverse dimension of the crotch region 7. If these angles θ1, θ2 exceed 120°, both the first folding guide lines 21 and the second folding guide lines 22 can not reach the waist lateral margins 10 and the contractile force of the first and second elastic members 24, 25 can not pull the first and second zones 21, 22 inward as viewed in the leg-surrounding direction. Consequently, it will be impossible to form the tucks 26, 27 in the crotch region 7.

The first and second zones 21, 22 respectively form the tucks 26, 27 which are convex inwardly of the leg-holes 15 so that these zones 21, 22 may rise toward the waist-hole 14, as seen in FIG. 4. These first and second zones 21, 22 rising in this manner form barriers against bodily discharges and reliably prevent any quantity of bodily discharges from leaking sideways from the first and second zones 21, 22. The reduced transverse dimension of the crotch region 7 does not adversely affect the bodily discharge absorbing function in the crotch region 7 since the portions of the core 4 lying in the first and second zones 21, 22 effectively absorb and retain bodily discharges.

The elastic members 18 contract inward as viewed in the leg-surrounding direction and cause the lateral margins 2b, 3b of the sheets 2, 3 to rise on the core 4 as the tucks 26, 27 are unfolded against the contractile force of the elastic members 24, 25. Even when the tucks 26, 27 are unfolded, the lateral margins 2b, 3b of these sheets 2, 3 rising above the core 4 form the barriers against bodily discharges and thereby prevent leak of bodily discharges from occurring around the crotch region 7.

Figure 5:
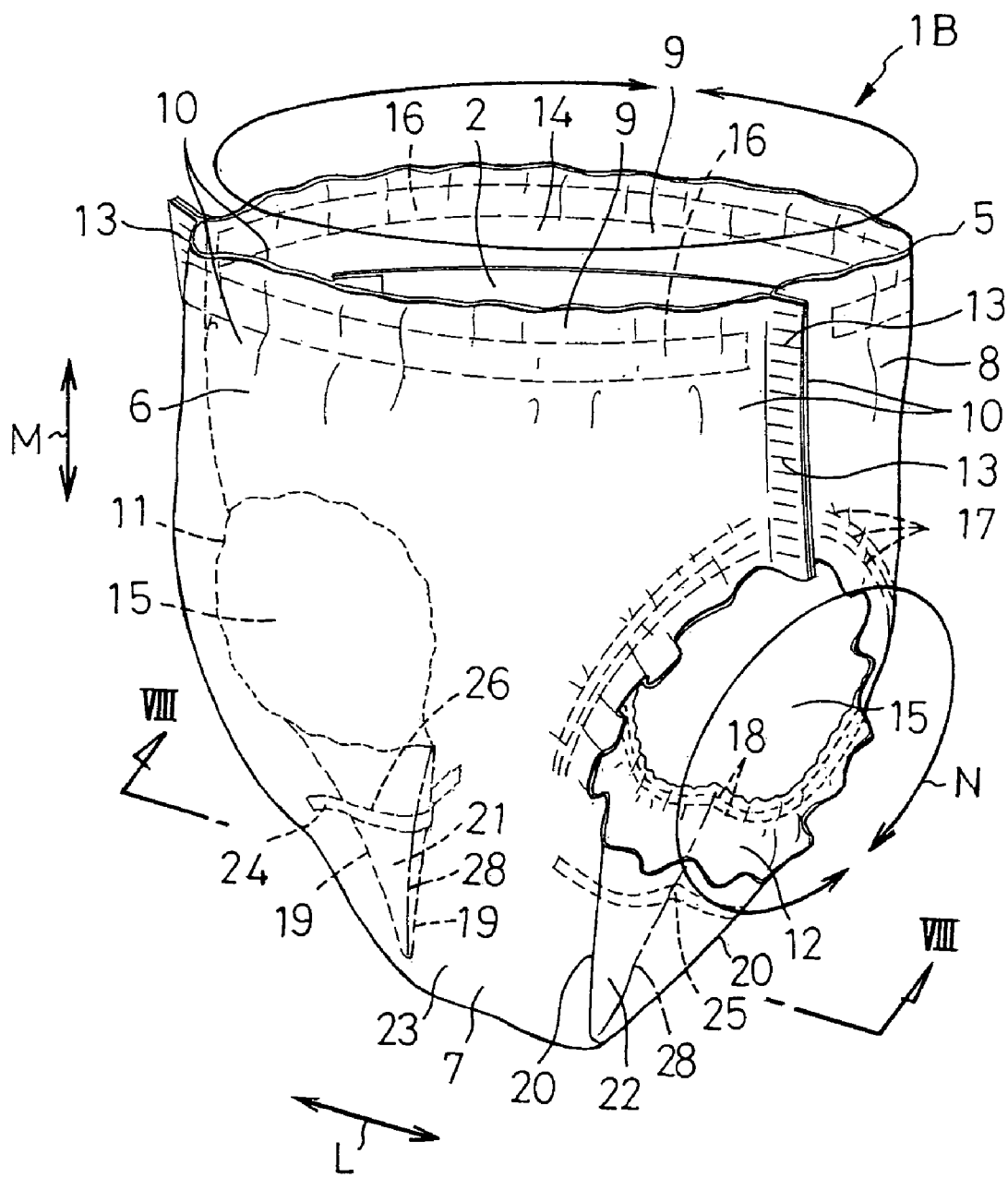
FIG. 5 is a perspective view showing a second embodiment of the wearing article according to the invention.
Figure 6:
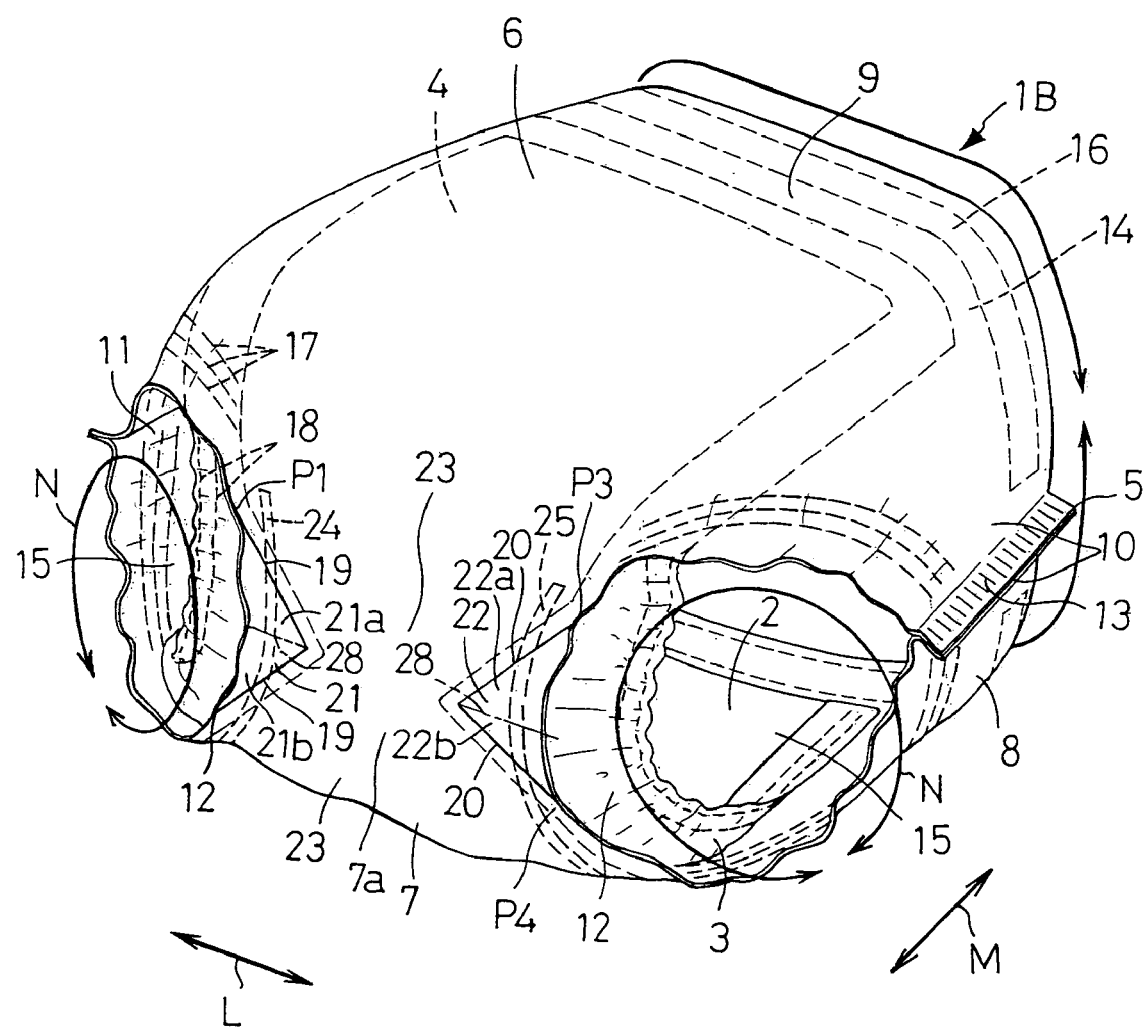
FIG. 6 is a perspective view showing the article of FIG. 5 as tucked regions unfolded outward against contractile force of elastic members.
Figure 7:
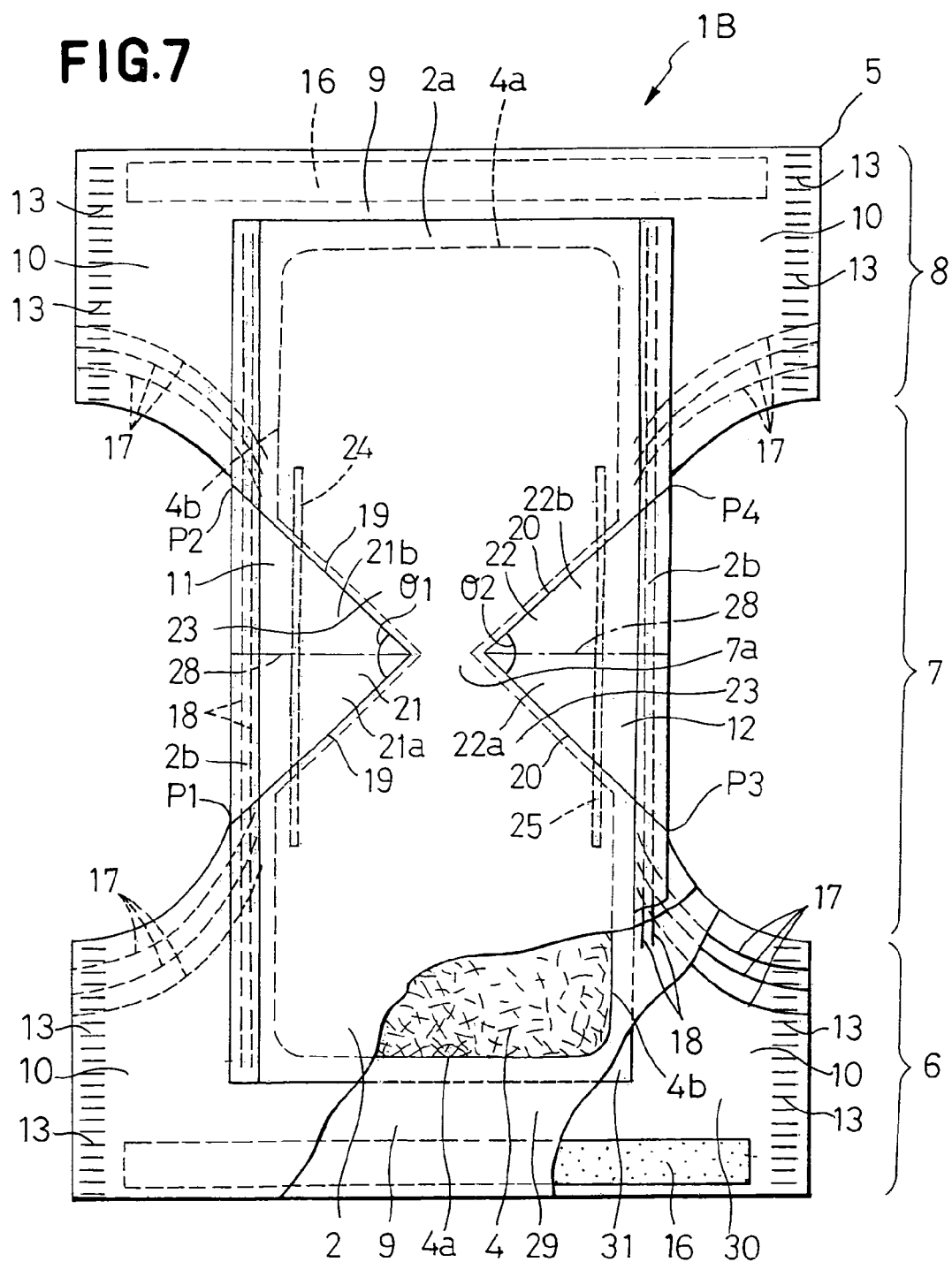
FIG. 7 is a partially cutaway developed plan view showing the article of FIG. 5 with front and rear waist regions disconnected from each other.

FIG. 5 is a perspective view showing a wearing article 1B according to a second embodiment of the invention, FIG. 6 is a perspective view showing the article 1B of FIG. 5 as tucks 26, 27 unfolded outward against contractile force of elastic members 24, 25, FIG. 3 is a developed plan view showing the article 1B of FIG. 5 with waist lateral margins 10 disconnected from each other as partially cutaway and FIG. 8 is a sectional view taken along the line VIII-VIII in FIG. 5. In FIGS. 5 through 7, a transverse direction is indicated by an arrow L, a longitudinal direction is indicated by an arrow M and a leg-surrounding direction is indicated by an arrow N (only in FIGS. 5 and 6). FIG. 7 shows the article 1B as stretched in the transverse direction as well as in the longitudinal direction.

The article 1B comprises the liquid-pervious topsheet 2 (liquid-pervious sheet), the liquid-impervious outer sheet 5 (liquid-impervious sheet), the liquid-absorbent core 4 interposed between these sheets 2, 5 and respective elastic members 16, 17, 18, 24, 25. The topsheet 2 faces a wearer's body with interposition of the core 4 and the outer sheet 5 faces away from a wearer's body. The article 1B has a front waist region 6 and a rear waist region 8 opposed to each other and a crotch region 7 extending between these waist regions 6, 8. The core 4 extends over the crotch region 7 and further into the front and rear waist regions 6, 8 so as to occupy transversely middle areas in these front and rear waist regions 6, 8.

The article 1B has a waist-surrounding upper margin 9 extending in the transverse direction, transversely opposite waist lateral margins 10 extending in the longitudinal direction, and first and second leg-surrounding lateral margins 11, 12 extending in the leg-surrounding direction. The first and second leg-surrounding lateral margins 11, 12 describe circular arcs which are convex inward as viewed in the transverse direction of the article 1B. The waist lateral margins 10 are overlapped and joined together by means of plural welding lines 13 arranged intermittently in the longitudinal direction. The article 1B is formed with a waist-hole 14 and a pair of leg-holes 15.

A belt-like waist elastic member 16 extending in the transverse direction is contractibly attached to the waist-surrounding upper margin 9. Plural leg elastic members 17, 18 are contractibly attached to the first and second leg-surrounding lateral margins 11, 12, respectively, so as to extend in the leg-surrounding direction.

As shown by FIG. 6, the crotch region 7 is formed with a pair of first folding guide lines 19 extending in the transverse direction from two points P1, P2 on the first leg-surrounding lateral margin 11 placed aside toward the front and rear waist regions 6, 8, respectively, toward a transverse middle 7a of the crotch region 7 and a pair of second folding guide lines 20 extending in the transverse direction from two points P3, P4 on the second leg-surrounding lateral margin 12 placed aside toward the front and rear waist regions 6, 8, respectively, toward the transverse middle 7a of the crotch region 7.

The crotch region 7 is divided into a first zone 21 enclosed by the first leg-surrounding lateral margin 11 and the first folding guide lines 19, a second zone 22 enclosed by the second leg-surrounding lateral margin 12 and the second folding guide-lines 20 and a third zone 23 except the first and second zones 21, 22. The first zone 21 has a generally triangular shape tapering from the first leg-surrounding lateral margin 11 toward the middle 7a of the crotch region 7. Similarly, the second zone 22 has a generally triangular shape tapering from the second leg-surrounding lateral margin 12 toward the middle 7a of the crotch region 7. The core 4 is absent in the first and second zones 21, 22.

Immediately inside the side edge 4b of the core 4 on the side of the first leg-surrounding lateral margin 11, a first elastic member 24 stretched at a predetermined ratio is contractibly attached to the article. The first elastic member 24 is laid inside the leg elastic members 18 as viewed in the transverse direction and extends in the leg-surrounding direction across the first zone 21 to the third zone 23. In the similar manner, immediately inside the side edge 4b of the core 4 on the side of the second leg-surrounding lateral margin 12, a second elastic member 25 stretched at a predetermined ratio is contractibly attached to the article. The second elastic member 25 is laid inside the leg elastic members 18 as viewed in the transverse direction and extends in the leg-surrounding direction across the second zone 22 to the third zone 23. The first and second elastic members 24, 25 are interposed between the topsheet 2 and the outer sheet 5 and bonded to the inner surfaces of these sheets 2, 5.

In the crotch region 7, the first zone 21 is pulled inward as viewed in the leg-surrounding direction under the contractile force of the first elastic member 24 and the second zone 22 is pulled inward as viewed in the leg-surrounding direction under the contractile force of the second elastic member 25 so that the crotch region 7 is folded along the first and second folding guide lines 19, 20. In the crotch region 7, consequently, the first zone 21 forms a tuck 26 which is convex inwardly of the leg-hole 15 and the second zone 22 forms a tuck 27 which is convex inwardly of the leg-hole 15. The first zone 21 and the second zone 22 are tucked between front and rear halves of the third zone 23. In the first zone 21, a front half 21a and a rear half 21b thereof contact each other while portions of the outer sheet 5 extending in these front and rear halves 21a, 21b of the first zone 21 have respective outer surfaces contacting each other. In the second zone 22 a front half 22a and a rear half 22b thereof contact each other while portions of the outer sheet 5 extending in these front and rear halves 22a, 22b of the second zone 22 have respective outer surfaces contacting each other. In the first and second zones 21, 22, imaginary third folding guide lines 28 extending in the transverse direction are defined between the front and rear halves 21a, 21b and between the front and rear halves 22a, 22b, respectively. An alternative case may be also assumed in which the zones 21, 22 are pulled inward as viewed in the leg-surrounding direction under the contractile force of the first and second elastic members 24, 25 and thereby these zones 21, 22 are tucked inwardly of the respective leg-holes 15 without forming the third folding guide lines 28 in these first and second zones 21, 22.

On the basis of 100 representing the length of these elastic members 24, 25 having been stretched at a predetermined ratio, the first and second elastic members 24, 25 exhibit the same contraction percentage and stretch stress as in the embodiment shown by FIG. 1.

The topsheet 2 has a generally rectangular planar shape extend over the crotch region 7 and further into the front and rear waist regions 6, 8. The topsheet 2 has longitudinally opposite end margins 2a, extending outward beyond the longitudinally opposite ends 4a of the core 4 and transversely opposite lateral margins 2b extending outward beyond the transversely opposite side edges 4b of the core 4. Inner surfaces of the top- and outer sheets 2, 5 are put flat and bonded together along these end margins 2a and lateral margins 2b. The core 4 is similar to the core in the embodiment shown by FIG. 1 and joined to the respective inner surfaces of the topsheet 2 and the outer sheet 5.

The outer sheet 5 comprises two hydrophobic fibrous nonwoven fabric layers 29, 30 laminated one upon another and a breathable liquid-impervious plastic film 31 interposed between these nonwoven fabric layers 29, 30. The outer sheet 5 has a surface area larger than the surface area of the topsheet 2 and has a generally hourglass-like planar shape. The film 31 also has a generally rectangular planar shape and generally the same as the topsheet 2 in shape as well as size and underlies the core 4. Of the outer sheet 5, the nonwoven fabric layers 29, 30 are partially overlapped and joined together and the film 31 is joined to these nonwoven fabric layers 29, 30. The waist-surrounding upper end margin 9 and the waist lateral margins 10 are formed by the outer sheet 5 and the leg-surrounding lateral margins 11, 12 are formed by the lateral margins 2b of the topsheet 2 and the outer sheet 5.

The waist elastic member 16 is interposed between the nonwoven fabric layers 29, 30 constituting the outer sheet 5 and bonded to these nonwoven fabric layers 29, 30. The leg elastic members 17, 18 comprise the elastic member 17 attached to the outer sheet 5 and the elastic member 18 attached to the topsheet 2. The elastic members 17 are interposed between the nonwoven fabric layers 29, 30 and attached to these nonwoven fabric layers 23, 30. The elastic members 18 are attached to the lateral margins 2b of the topsheet 2 so that these elastic members 18 may be wrapped with a part of the topsheet 2.

The article 1B is constructed so that, in the crotch region 7, the first and second zones 21, 22 form the tucks 26, 27 which are convex inwardly of the leg-holes 15 and therefore a transverse dimension of the crotch region 7 is correspondingly reduced. The contractile force of the first and second elastic members 24, 25 reliably stabilizes the tucks 26, 27 and it is unlikely that these tucks 26, 27 might be unintentionally unfolded even when a wearer's legs are guided through the leg-holes 15.

The crotch region 7 is appropriately received in a wearer's crotch region as the article 1B is put on a wearer's body, so there is no possibility that the crotch region 7 might become excessively bulky and a wearer might experience a feeling of incompatibility. In addition, there is no anxiety that the core 4 in the crotch region 7 might be irregularly folded and/or formed with a plurality of irregular wrinkles even if the crotch region 7 is squeezed in a wearer's crotch region. Thus, bodily discharges absorbing function in the crotch region 7 is reliably maintained without any possibility that the bodily discharges might leak sideways from the crotch region 7. In the article 1B, an angle θ1 defined between the first folding guide lines 19 as well as an angle θ2 defined between the second folding guide lines 20 is preferably in a range of 30 to 120° as shown by FIG. 6.

The first and second zones 21, 22 form the tucks 26, 27 which are convex inwardly of the leg-holes 15 and rise toward the waist-hole 14, as will be apparent from FIG. 8. These zones 21, 22 rising in this manner form the barriers against bodily discharges and thereby prevent leak of bodily discharges from occurring around the crotch region 7.

Stock materials for the topsheet 2 may be selected from a hydrophilic fibrous nonwoven fabric, a hydrophobic fibrous nonwoven fabric having a plurality of apertures and a plastic film having a plurality of fine apertures. Stock materials for the intermediate sheet 3 may be selected from a hydrophilic fibrous nonwoven fabric, a hydrophobic fibrous nonwoven fabric and a breathable liquid-impervious plastic film. It is also possible to use, as stock materials for the intermediate sheet 3 and the outer sheet 5, a composite nonwoven fabric comprising a melt blown fibrous nonwoven fabric having a high water-resistance and a spun bond fibrous nonwoven fabric having a high strength as well as a high flexibility laminated on at least one side of the melt blown fibrous nonwoven fabric.

Nonwoven fabrics used for the present invention may be selected from spun lace-, needle punch-, melt blown-, thermal bond-, spun bond-, and chemical bond-processes. Component fibers of the nonwoven fabric may be selected from polyolefin-, polyester- and polyamide-fibers, and core-and-sheath type or side-by-side type conjugate fibers of polyethylene/polypropylene or polyethylene/polyester.

Stock materials for the outer sheet 5 may be selected from a elastically stretchable hydrophobic fibrous nonwoven fabric, an elastically stretchable breathable liquid-impervious plastic film and a composite sheet comprising an elastically stretchable hydrophobic fibrous nonwoven fabric laminated with an elastically stretchable breathable liquid-impervious plastic film. It is possible to use, as the outer sheet, a composite nonwoven fabric comprising an elastically stretchable hydrophobic fibrous nonwoven fabric made of thermoplastic elastomeric resin fibers, and a hydrophobic fibrous nonwoven fabric made of crimped fibers obtained by melt spinning thermoplastic synthetic resin of polypropylene, polyethylene or polyester, laminated at least one side of the former fibrous nonwoven fabric.

Joining of the sheets 2, 3, 5 one to another, joining of the core 4 to the sheets 2, 3, 5 and joining of the elastic members 16, 17, 18, 24, 25 to the sheets 2, 3, 5 may be achieved using hot melt adhesives or welding techniques such as heat-sealing or sonic-sealing techniques.

The pull-on disposable wearing article according to the present invention is primarily characterized in that, in the crotch region, the first and second zones form the tucks which are convex inwardly of the leg-holes and therefore a transverse dimension of the crotch region can be reduced than in the case of the crotch region not formed with such tucks. In the article, the contractile force of the first and second elastic members reliably stabilizes the tucks and it is unlikely that these tucks might be unintentionally unfolded even when a wearer's legs are guided-through the leg-holes.

The crotch region is appropriately received in a wearer's crotch region as the article is put on a wearer's body, so there is no possibility that the crotch region might become excessively bulky and the wearer might experience a feeling of discomfort. In addition, there is no anxiety that the core in the crotch region might be irregularly folded and/or formed with a plurality of irregular wrinkles even if the crotch region is squeezed in a wearer's crotch region. Therefore, bodily discharges absorbing function in a crotch region is reliably maintained without any possibility that the bodily discharges might leak sideways from the crotch region.

In the embodiments of the article wherein the core has stiffness lower in the first and second zones than in the third zone, a contractile force of the first and second elastic members is sufficiently high to pull the first and second zones inwardly of the leg-holes and thereby to facilitate the tucks to be formed in the crotch region.

In the embodiments of the article wherein the core is absent in the first and second zones, a contractile force of the first and second elastic members can smoothly pull the first and second zones inwardly of the leg-holes without being affected by stiffness of the core and thereby to facilitate the tucks to be formed in the crotch region.

What is claimed is:

1. A pull-on disposable wearing article, comprising:
    front and rear waist regions opposed to each other and a crotch region extending between said waist regions;
    a waist-surrounding upper end margin defined by said front and rear waist regions and extending in a transverse direction of said article;
    transversely opposite waist lateral margins defined by said front and rear waist regions and extending in a longitudinal direction of said article, wherein said waist lateral margins of said front and rear waist regions are connected to form a waist-hole and first and second leg-holes;
    first and second leg-surrounding lateral margins defined by said crotch region and extending in leg-surrounding directions of the first and second leg holes, respectively;
    a liquid-absorbent core laid in said front waist region, said rear waist region and said crotch region, or at least in said crotch region;
    said crotch region being formed with
        a pair of first folding guide lines extending from two points on said first leg-surrounding lateral margin adjacent said front and rear waist regions, respectively, toward a transverse middle of said crotch region, and
        a pair of second folding guide lines extending from two points on said second leg-surrounding lateral margin adjacent said front and rear waist regions, respectively, toward said transverse middle of said crotch region, so that said crotch region is divided into
        a first zone enclosed by said first leg-surrounding lateral margin and said first folding guide lines so as to taper toward said transverse middle of said crotch region,
        a second zone enclosed by said second leg-surrounding lateral margin and said second folding guide lines so as to taper toward said transverse middle of said crotch region, and
        a third zone except said first and second zones;
    a first elastically stretchable and contractible member extending in the leg-surrounding direction of the first leg hole across said first zone into said third zone, wherein said first elastically stretchable and contractible member is contractibly attached to the article inboard of a first longitudinal side edge of said core adjacent said first leg-surrounding lateral margin, and
    a second elastically stretchable and contractible member extending in the leg-surrounding direction of the second leg hole across said second zone into said third zone, wherein said second elastically stretchable and contractible member is contractibly attached to the article inboard of a second longitudinal side edge of said core adjacent said second leg-surrounding lateral margin; and
    wherein
    said first zone is pulled inward as viewed in the respective leg-surrounding direction under a contractile force of said first elastically stretchable and contractible member to form a first tuck which is convex inwardly of said first leg-hole, and
    said second zone is pulled inward as viewed in the respective leg-surrounding direction under a contractile force of said second elastically stretchable and contractible member to form a second tuck which is convex inwardly of said second leg-hole.

2. The wearing article according to claim 1, wherein said first and second elastically stretchable and contractible members exhibit a contraction percentage in a range of 25 to 70% on the basis of 100 representing a length of said first and second elastically stretchable and contractible members having been stretched at a predetermined ratio.

3. The wearing article according to claim 1, wherein said first and second elastically stretchable and contractible members exhibit a stretch stress in a range of 0.1 to 3.0 N.

4. The wearing article according to claim 1, wherein a stiffness of said core in said first and second zones and outside said folding guide lines is lower than in said third zone.

5. A pull-on disposable wearing article comprising:
    front and rear waist regions opposed to each other and a crotch region extending between said waist regions;
    a waist-surrounding upper end margin defined by said front and rear waist regions and extending in a transverse direction;
    transversely opposite waist lateral margins defined by said front and rear waist regions and extending in a longitudinal direction so that said waist lateral margins of said front and rear waist regions are connected to form a waist-hole and a pair of leg-holes;
    first and second leg-surrounding lateral margins defined by said crotch region and extending in a leg-surrounding direction;
    a liquid-absorbent core laid in said front waist region, said rear waist region and said crotch region, or at least in said crotch region;
    said crotch region being formed with a pair of first folding guide lines extending from two points on said first leg-surrounding lateral margin placed aside toward said front and rear waist regions, respectively, toward a transverse middle of said crotch region and a pair of second folding guide lines extending from two points on said second leg-surrounding lateral margin placed aside toward said front and rear waist regions, respectively, toward said transverse middle of said crotch region so that said crotch region is divided into a first zone enclosed by said first leg-surrounding lateral margin and said first folding guide lines so as to taper toward said transverse middle of said crotch region, a second zone enclosed by said second leg-surrounding lateral margin and said second folding guide lines so as to taper toward said transverse middle of said crotch region and a third zone except said first and second zones;
    a first elastically stretchable and contractible member extending in the leg-surrounding direction across said first zone to said third zone is contractibly attached to the article inside the side edge of said core on the side of said first leg-surrounding lateral margin and a second elastically stretchable and contractible member extending in the leg-surrounding direction across said second zone to said third zone is contractibly attached to the article inside the side edge of said core on the side of said second leg-surrounding lateral margin; and said first zone being pulled inward as viewed in the leg-surrounding direction under a contractile force of said first elastically stretchable and contractible member to form a tuck which is convex inwardly of said leg-hole and said second zone is pulled inward as viewed in the leg-surrounding direction under a contractile force of said second elastically stretchable and contractible member to form a tuck which is convex inwardly of said leg-hole;

wherein said core is absent in said first and second zones.

6. The wearing article according to claim 1, wherein said article comprises a liquid-pervious sheet facing a wearer's body, a liquid-impervious sheet facing away from the wearer's body and said core interposed between these sheets.

7. The wearing article according to claim 1, further comprising two longitudinal bafflers disposed on opposite sides of said core to prevent lateral leakage of bodily discharge, wherein said first and second elastically stretchable and contractible members are disposed between and inwardly spaced from entireties of said longitudinal barriers.

8. The wearing article according to claim 1, wherein said first and second elastically stretchable and contractible members are disposed below said core, between said core and an impervious cover sheet covering a lower surface of said core.

9. The wearing article according to claim 8, wherein each of said first and second elastically stretchable and contractible members is directly attached to said core.

10. The wearing article according to claim 1, wherein said first and second elastically stretchable and contractible members are shorter than said core as measured in the longitudinal direction of said article.

11. The wearing article according to claim 1, wherein said core is folded along said folding guide lines and is present in the tucks formed by said first and second zones.

12. The wearing article according to claim 9, further comprising:
    a liquid-pervious top sheet adapted to face a wearer's body in use, and
    a liquid-impervious back sheet adapted to face away from the wearer's body in use, wherein
    said core is interposed between said top sheet and back sheet; and
    said first and second elastically stretchable and contractible members are disposed between said back sheet and said core, and are free of direct attachment to said topsheet.

13. The wearing article according to claim 1, wherein said core is absent in said tucks.

14. The wearing article according to claim 1, wherein said core is absent in portions of the first and second zones that are outside said folding guide lines.

15. A pull-on disposable wearing article, comprising:
    front and rear waist regions and a crotch region extending between said waist regions;
    a waist-surrounding upper end margin defined by said front and rear waist regions and extending in a transverse direction of said article;
    transversely opposite waist lateral margins defined by said front and rear waist regions and extending in a longitudinal direction of said article, wherein said waist lateral margins of said front and rear waist regions are connected to form a waist-hole and first and second leg-holes;
    first and second leg-surrounding lateral margins defined by said crotch region and extending in leg-surrounding directions of the first and second leg holes, respectively, to define peripheral edges of the first and second leg holes, respectively;
    a liquid-absorbent core laid in at least said crotch region and having first and second longitudinal side edges adjacent said first and second leg-surrounding lateral margins, respectively;
    said crotch region being formed with
       a pair of first folding guide lines extending from a middle of said crotch region to said first leg-surrounding lateral margin and toward said front and rear waist regions, respectively, and
       a pair of second folding guide lines extending from said middle of said crotch region to said second leg-surrounding lateral margin and toward said front and rear waist regions, respectively,
    wherein said crotch region is divided into
       a first zone enclosed by said first leg-surrounding lateral margin and said first folding guide lines and tapering toward said middle of said crotch region,
       a second zone enclosed by said second leg-surrounding lateral margin and said second folding guide lines and tapering toward said middle of said crotch region, and
       a third zone outside said first and second zones;
    a first elastically stretchable and contractible member extending in the leg-surrounding direction of the first leg hole across said first zone into said third zone; and
    a second elastically stretchable and contractible member extending in the leg-surrounding direction of the second leg hole across said second zone into said third zone;
    wherein said first and second elastically stretchable and contractible members are located between and inwardly spaced from the first and second longitudinal side edges of said core as seen in the transverse direction of the article; and
    wherein said first and second zone are pulled inward under contractile forces of said first and second elastically stretchable and contractible members, respectively, to form first and second tucks, respectively.

16. The wearing article according to claim 15, wherein a basic weight or density of said core in said first and second zones and outside said folding guide lines is lower than in said third zone.

17. The wearing article according to claim 15, wherein said core is absent in entire said first and second zones.

18. The wearing article according to claim 15, wherein each of said first and second elastically stretchable and contractible members is directly attached to said core.

19. The wearing article according to claim 15, further comprising:
    a liquid-pervious top sheet adapted to face a wearer's body in use, and
    a liquid-impervious back sheet adapted to face away from the wearer's body in use, wherein
    said core is interposed between said top sheet and back sheet; and
    said first and second elastically stretchable and contractible members are disposed between said back sheet and said core.

20. The wearing article according to claim 19, wherein each of said first and second elastically stretchable and contractible members is directly attached to said core and free of direct attachment to said topsheet.

* * * * *